(12) United States Patent
Filbin et al.

(10) Patent No.: US 8,598,315 B2
(45) Date of Patent: Dec. 3, 2013

(54) PROTEIN TRANSDUCTION DOMAINS DERIVED FROM SECRETORY LEUKOCYTE PROTEASE INHIBITOR

(75) Inventors: Marie T. Filbin, New York, NY (US); Sari S. Hannila, New York, NY (US)

(73) Assignee: Research Foundation of City University of New York, New York, NY (US)

(*) Notice: Subject to any disclaimer, the term of this patent is extended or adjusted under 35 U.S.C. 154(b) by 414 days.

(21) Appl. No.: 12/681,243

(22) PCT Filed: Oct. 2, 2008

(86) PCT No.: PCT/US2008/011466
§ 371 (c)(1),
(2), (4) Date: Dec. 28, 2010

(87) PCT Pub. No.: WO2009/045508
PCT Pub. Date: Apr. 9, 2009

(65) Prior Publication Data
US 2011/0107443 A1  May 5, 2011

Related U.S. Application Data

(60) Provisional application No. 60/997,430, filed on Oct. 2, 2007.

(51) Int. Cl.
*A61K 38/04* (2006.01)
*A61K 38/10* (2006.01)
*C07K 7/08* (2006.01)

(52) U.S. Cl.
USPC .................................................. 530/326

(58) Field of Classification Search
USPC ........................................................ 530/326
See application file for complete search history.

(56) References Cited

U.S. PATENT DOCUMENTS

2004/0106120 A1*  6/2004  Tazi-Ahnini et al. ............. 435/6

FOREIGN PATENT DOCUMENTS

WO    WO 96/08275 A    3/1996

OTHER PUBLICATIONS

Masuda et al, Protein Eng. 9(1):101-106, 1996.*
Stetler et al, GenBank CAA28187.1; 2005.*
Stetler et al, Nature Biotechnology 7:55-60, 1989.*
Taggart et al., "Secretory Leucoprotease Inhibitor Binds to NF-Kappa Beta Binding Sites in Monocytes and Inhibits P65 Binding" Journal of Experimental Medicine, vol. 202, No. 12, pp. 1659-1668 (Dec. 2005).
Masuda et al., "Pharmacological Activity of the C-Terminal and N-Terminal Domains of Secretory Leukoprotease Inhibitors in Vitro", British Journal of Pharmacology, vol. 115, No. 6, pp. 883-888 (Jan. 1995).

* cited by examiner

*Primary Examiner* — Kevin Hill
(74) *Attorney, Agent, or Firm* — Hoffmann & Baron, LLP

(57) ABSTRACT

This invention relates to novel protein transduction domains (PTDs) derived from secretory leukocyte protease inhibitor (SLPI). SLPI-derived PTDs are able to deliver cargo moieties in vivo and in vitro into the cytoplasm and nucleus of a host cell. The invention also relates to a transduction complex comprising one or more SLPI-derived PTDs linked or fused to one or more cargo moieties, which may comprise, for example, proteins, nucleic acids, lipids, carbohydrates, small molecules and other chemical compounds. The invention also relates to the manufacture of SLPI-derived PTDs, complexes comprising them; compositions comprising SLPI-derived PTDs or complexes; and utilization of SLPI-derived PTDs or complexes comprising them for therapeutic, diagnostic and research methods involving delivery of heterologous molecules across cellular membranes, and especially, across nuclear membranes.

4 Claims, 6 Drawing Sheets

SEQUENCE LISTING

```
<160> NUMBER OF SEQ ID NOS: 6

<210> SEQ ID NO 1
<211> LENGTH: 107
<212> TYPE: PRT
<213> ORGANISM: Homo sapiens

<400> SEQUENCE: 1

Ser Gly Lys Ser Phe Lys Ala Gly Val Cys Pro Pro Lys Ser Ala
 1               5                  10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
            35                  40                  45

Asp Pro Val Asp Thr Pro Asn Pro Thr Arg Arg Lys Pro Gly Lys Cys
        50                  55                  60

Pro Val Thr Tyr Gly Gln Cys Leu Met Leu Asn Pro Asn Phe Cys
 65                 70                  75                  80

Glu Met Asp Gly Gln Cys Lys Arg Asp Leu Lys Cys Cys Met Gly Met
                85                  90                  95

Cys Gly Lys Ser Cys Val Ser Pro Val Lys Ala
            100                 105

<210> SEQ ID NO 2
<211> LENGTH: 15
<212> TYPE: PRT
<213> ORGANISM: Homo sapiens

<400> SEQUENCE: 2

Pro Pro Lys Lys Ser Ala Gln Cys Leu Arg Tyr Lys Lys Pro Glu
 1               5                  10                  15

<210> SEQ ID NO 3
<211> LENGTH: 15
<212> TYPE: PRT
<213> ORGANISM: Homo sapiens

<400> SEQUENCE: 3

Asp Pro Val Asp Thr Pro Asn Pro Thr Arg Arg Lys Pro Gly Lys
```

<210> SEQ ID NO 4
<211> LENGTH: 54
<212> TYPE: PRT
<213> ORGANISM: Homo sapiens

<400> SEQUENCE: 4

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro
    50

<210> SEQ ID NO 5
<211> LENGTH: 53
<212> TYPE: PRT
<213> ORGANISM: Homo sapiens

<400> SEQUENCE: 5

Asn Pro Thr Arg Arg Lys Pro Gly Lys Cys Pro Val Thr Tyr Gly Gln
1               5                   10                  15

Cys Leu Met Leu Asn Pro Pro Asn Phe Cys Glu Met Asp Gly Gln Cys
            20                  25                  30

Lys Arg Asp Leu Lys Cys Cys Met Gly Met Cys Gly Lys Ser Cys Val
        35                  40                  45

Ser Pro Val Lys Ala
    50

<210> SEQ ID NO 6
<211> LENGTH: 50
<212> TYPE: PRT
<213> ORGANISM: Homo sapiens

<400> SEQUENCE: 6

Arg Arg Lys Pro Gly Lys Cys Pro Val Thr Tyr Gly Gln Cys Leu Met
1               5                   10                  15

Leu Asn Pro Pro Asn Phe Cys Glu Met Asp Gly Gln Cys Lys Arg Asp
            20                  25                  30

Leu Lys Cys Cys Met Gly Met Cys Gly Lys Ser Cys Val Ser Pro Val
        35                  40                  45

Lys Ala
    50

PROTEIN TRANSDUCTION DOMAINS DERIVED FROM SECRETORY LEUKOCYTE PROTEASE INHIBITOR

REFERENCE TO SEQUENCE LISTING

Pursuant to 37 C.F.R. 1.821(c), a sequence listing is submitted herewith as an ASCII compliant text file named "Sequence Listing.txt" that was created on Dec. 28, 2010, and has a size of 3083 bytes. The content of the aforementioned file named "Sequence Listing.txt" is hereby incorporated by reference in its entirety.

TECHNICAL FIELD OF THE INVENTION

This invention relates to the use of secretory leukocyte protease inhibitor ("SLPI") and sequences derived from SLPI as protein transduction domains, also known as cell penetrating peptides, useful for transporting heterologous molecules across membranes, such as cellular membranes and especially across nuclear membranes of the cell.

BACKGROUND OF THE INVENTION

Cells are generally impermeable to macromolecules such as proteins, nucleic acids, lipids, carbohydrates and other chemical compounds. Methods for efficient translocation of these agents across biological membranes are thus useful for both therapeutic and research applications. However, existing methods of intracellular delivery, such as electroporation, liposome fusion, gene gun particle bombardment, DEAE-dextran transfection, recombinant viral infection, and direct microinjection are often inefficient and/or toxic to cells. Accordingly, there is a continuing need for improved intracellular delivery methods, including methods that can be used for in vivo delivery of agents such as proteins, nucleic acids, lipids, carbohydrates, small molecules and other chemical compounds.

Studies have identified polypeptide sequences known as protein transduction domains (PTDs) that may serve this need. PTDs, also known as "cell penetrating peptides" (CPPs), possess the ability to translocate across biological membranes. PTDs are relatively short amino acid sequences that can be linked to a cargo moiety, allowing transport of the cargo moiety across a biological membrane, such as a cell membrane, an organelle membrane, and/or a nuclear membrane. Cargo moieties can include, for example, small molecules, macromolecules, lipids, liposomes, carbohydrates, proteins, or nucleic acids. While the mechanism of translocation remains unclear, some studies suggest that the mechanism is energy-independent and non-receptor-mediated (Derossi et al., *J. Biol. Chem.* 269:10444-50 (1994); Derossi et al., *J. Biol. Chem.* 271:18188-93 (1996); Vives et al., *J. Biol. Chem.* 272:16010-7 (1997); Nagahara et al., *Nat. Med.* 4:1449-52 (1998); Schwarze et al., *Trends Cell Biol.* 10:290-5 (2000)). Other studies suggest that PTDs operate through pinocytotic mechanisms (Leifert et al., *Gene Ther.* 9:1422-8 (2002); Fittipaldi et al., *J. Biol. Chem.* 278:34141-9 (2003); Whitton and Whitton, *Mol. Ther.* 8:13-20 (2003); Lundberg et al., *Mol. Ther.* 8:143-50 (2003); Richard et al., *J. Biol. Chem.* 278:585-90 (2003); Vives et al., *Curr. Protein Pept. Sci.* 4:125-32 (2003)).

PTDs are typically cationic in nature, often comprising, for example, multiple arginines or lysines. Naturally occurring PTDs have been derived from proteins which can efficiently pass through biological membranes. The best characterized of these PTDs are derived from the *Drosophila* homeoprotein antennapedia transcription protein (AntHD) (Joliot et al., *New Biol.* 3:1121-34 (1991); Joliot et al., *Proc. Natl. Acad. Sci. USA* 88:1864-8 (1991); Le Roux et al., *Proc. Natl. Acad. Sci. USA,* 90:9120-4 (1993); Derossi et al., *Trends Cell Biol.* 8:84-87 (1998)), the herpes simplex virus structural protein VP22 (Elliott and O'Hare, *Cell* 88:223-33 (1997); Elliot et al., *Cell* 88:223-233 (1997)) and the HIV-1 transcriptional activator TAT protein (Green and Loewenstein, *Cell* 55:1179-1188 (1988); Frankel and Pabo, *Cell* 55:1189-1193 (1988); U.S. Pat. Nos. 5,804,604; 5,747,641; 5,674,980; 5,670,617; and 5,652,122). Recent studies have also identified other PTDs, such as Mph-1 (U.S. Patent Application No. 20060148060); Sim-2 (Chrast et al., *Genome Res.* 7, 615-624 (1997)); and Pep-1 and Pep-2 (Morris et al., *Nat. Biotech.* 19:1173-1175 (2001)), among others. In addition, studies have isolated artificial PTDs and PTDs selected from random libraries (see, e.g., Joliot and Prochiantz, *Nat. Cell Biol.* 6(3): 189-96 (2004); Zhao and Weissleder, *Med. Res. Rev.* 24(1): 1-12 (2003); Saalik et al., *Bioconj. Chem.* 15:1246-1253 (2004)).

PTD-mediated translocation appears to circumvent many of the problems and limitations associated with other techniques of intracellular delivery. This method of transduction appears to work on all cell types, and has been shown to efficiently transduce up to 100% of cells in culture with no apparent toxicity (Nagahara et al., *Nat. Med.* 4:1449-52 (1998)). PTDs have been used successfully to induce the intracellular uptake of full-length proteins (Nagahara et al., *Nat. Med.* 4:1449-52 (1998)), DNA, antisense oligonucleotides (Astriab-Fisher et al., *Pharm. Res.,* 19:744-54 (2002)), small molecules (Polyakov et al., *Bioconjug. Chem.* 11:762-71 (2000)) and even inorganic iron particles (Dodd et al., *J. Immunol. Methods* 256:89-105 (2001); Wunderbaldinger et al., *Bioconjug. Chem.* 13:264-8 (2002); Lewin et al., *Nat. Biotechnol.* 18:410-4 (2000); Josephson et al., *Bioconjug. Chem.* 10:186-91 (1999)) suggesting that there is no apparent limit to the size of molecules that can be translocated.

Due to the many advantages of PTD-mediated intracellular delivery, there is a continuing need in the art to identify and characterize new PTDs. It would be useful to have new PTDs capable of efficiently and effectively translocating a variety of different types of cargo moieties across cellular membranes and thus useful for a multitude of therapeutic, diagnostic and research methods which require targeted delivery of cargo moieties into a cell or into one or more specific locations within a cell. Further, it would be especially useful to identify PTDs that can cross not only the outer cell membrane, but also the nuclear membrane. Such PTDs would be useful, for example, for gene therapy applications, or for in vitro or in vivo transfection of cells.

SLPI is a serine protease inhibitor that plays an important role in protection of the mucosal epidermis and skin (Thompson et al., *Proc. Natl. Acad. Sci. USA* 83:6692-6696 (1986); Franken et al., *J. Histochem. Cytochem.* 37:493-498 (1989); Masuda et al., *British J. Pharmacol.* 115:883-888 (1995)). SLPI is a potent inhibitor of leukocyte serine proteases such as elastase and cathepsin G from neutrophils, and chymase and tryptase from mast cells, as well as trypsin and chymotrypsin from pancreatic acinar cells (Jin et al., *Cell* 88:417-26 (1997) and references cited therein; Grüter et al., *EMBO* 7:345-51 (1988)). Studies suggest that SLPI also functions in wound healing (Zhu et al., *Cell* 111:867-878 (2002)) and epithelial proliferation (Zhang et al., *J. Biol. Chem.* 277: 29999-30009 (2002)), and has antibacterial, antiviral and anti-inflammatory properties (McNeely et al., *J. Clin. Invest.*

96:456-464 (1995); Song et al., *J. Exp. Med.* 190:535-542 (1999); Hiemstra et al., *Curr. Pharm. Des.* 10:2891-2905 (2004)).

Human SLPI is a nonglycosylated, 11.7 kD protein consisting of a single 107 amino acid polypeptide chain. SLPI comprises two cysteine-rich domains with a protease inhibitory site situated at leucine 72 in the carboxy-terminal domain. SLPI is found in parotid saliva, and in seminal plasma, cervical, nasal, and bronchial mucus. In human epithelial cells, SLPI is constitutively expressed and its expression is increased by phorbol ester, TNF-α, and LPS at supraphysiologic concentrations, as well as by synergistic combinations of elastase and corticosteroids (Jin et al., supra).

In the immune system, studies show SLPI to be a lipopolysaccharide (LPS)-induced, IFNγ-suppressible phagocyte product that inhibits LPS responses. SLPI binds to the membrane of human macrophages through annexin II (Jin et al., supra; Ma et al., *J. Exp. Med.* 200:1337-46 (2004)). SLPI binds to NF-κB binding sites in the promoter regions of the IL-8 and TNF-α genes in monocytes and inhibits the expression of those genes (Taggart et al., *J. Exp. Med.* 202:1659-68 (2005) and references cited therein). It has been suggested that the anti-inflammatory function of SLPI arises from such gene inhibition.

Recent studies suggest that SLPI may play a neuroprotective role in focal stroke because of rapid inhibition of activated proteases and its suppression in inflammatory response mediated by leukocytes (e.g., neutrophils and macrophages), which contributes to ischemic brain injury (Taggart et al., supra; Ilzecka et al., *Cerebrovascular Diseases* 13:38-42 (2002)). Elevated levels of serum SLPI are also observed in human stroke patients (Ilzecka et al., supra).

We previously discovered that secretory leukocyte protease inhibitor ("SLPI") overcomes the inhibitory effect of myelin inhibitors on nerve fiber growth and promotes neuronal (e.g., axonal) regeneration. Before that discovery, it was not known that SLPI possesses neurostimulatory function. See PCT/US2007/008270, filed Mar. 30, 2007, which is incorporated by reference herein in its entirety.

Upon incubation with peripheral blood monocytes and the U937 monocytic cell line, SLPI has been shown to enter cells, becoming rapidly localized to the cytoplasm and nucleus (Taggart et al., supra). But the portions of SLPI necessary and sufficient for cellular localization of SLPI were not known. Nor was it known whether part or all of the amino acid sequences of SLPI could be linked to a cargo moiety and co-transport that moiety across one or more biological membranes.

SUMMARY OF THE INVENTION

The present invention describes for the first time new PTDs derived from secretory leukoprotease inhibitor (SLPI). The present invention provides, in part, SLPI-derived amino acid sequences that function as protein transduction domains (PTDs). These SLPI-derived PTDs may be used to transport proteins, nucleic acids, lipids, carbohydrates, small molecules and other chemical compounds (collectively referred to herein as "cargo moieties") efficiently across biological membranes and may be used, for example, for targeted delivery of such cargo moieties to the cytoplasm and nucleus of cells in vivo and in vitro. SLPI-derived PTDs of the invention may be used to target molecules to the cytoplasm and/or nucleus of a cell and are thus useful in therapeutic and diagnostic, as well as research methods.

The invention further provides a transduction complex comprising one or more SLPI-derived PTDs linked or fused to one or more cargo moieties, which may comprise, for example, proteins, nucleic acids, lipids, carbohydrates, small molecules and other chemical compounds.

The invention also provides nucleic acid molecules encoding SLPI-derived PTDs, wherein a nucleic acid molecule may, in some embodiments, be operably linked to a nucleic acid molecule that is itself or that encodes one or more cargo moieties.

The invention provides vectors comprising the nucleic acid molecules, as well as methods of recombinantly producing the polypeptides encoded by the nucleic acid molecules.

The invention further provides a host cell or an isolated cell line that produces one or more SLPI-derived PTDs, optionally linked to one or more cargo moieties.

Non-human transgenic animals or plants that express SLPI-derived PTDs are also provided.

The invention also provides a composition comprising one or more SLPI-derived PTDs, or nucleic acid molecules encoding one or more SLPI-derived PTDs of the invention, and a pharmaceutically acceptable carrier. Compositions of the invention may further comprise other components, such as one or more non-SLPI-derived therapeutic, diagnostic, or research agents.

Therapeutic, diagnostic and research methods are also provided by the invention, the methods including the step of administering a SLPI-derived PTD comprising compound or composition to a cell or a subject in need of at least one cargo moiety that is or which can subsequently be linked thereto.

DETAILED DESCRIPTION OF THE INVENTION

Figure 1:
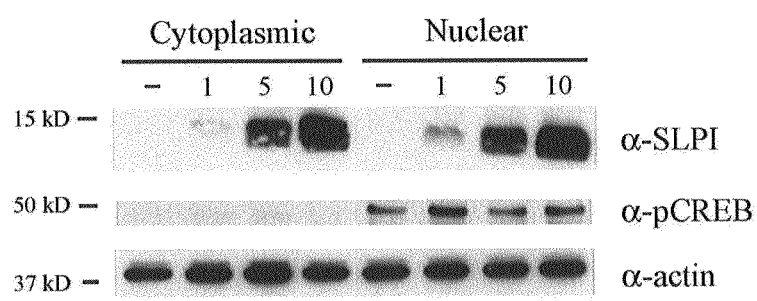
FIG. 1: Western blot analysis of cytoplasmic and nuclear fractions from cerebellar neurons treated with 0, 1, 5, and 10 µg/ml SLPI for 1 hour. Higher levels of SLPI are observed in both cytoplasmic and nuclear fractions with increasing concentrations of SLPI. Phospho-CREB is used as a nuclear marker and actin is used as a loading control. See Example 1.

In order that the invention herein described may be fully understood, the following detailed description is set forth.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. In general, terms used in connection with, and techniques of, cell and tissue culture, molecular biology, immunology, microbiology, genetics and protein and nucleic acid chemistry and hybridization described herein are those well known and commonly used in the art. Although methods and materials similar or equivalent to those described herein can be used in the practice or testing of the present invention, suitable methods and materials are described below. The materials, methods and examples are illustrative only, and are not intended to be limiting.

The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2nd ed., Cold Spring Harbor Laboratory Press, Cold Spring Harbor, N.Y. (1989); Sambrook et al., *Molecular Cloning: A Laboratory Manual,* 3rd ed., Cold Spring Harbor Press (2001); Ausubel et al., *Current Protocols in Molecular Biology,* Greene Publishing Associates (1992, and Supplements to 2001); Ausubel et al., *Short Protocols in Molecular Biology: A Compendium of Methods from Current Protocols in Molecular Biology,* $4^{th}$ Ed., Wiley & Sons (1999); Harlow and Lane, *Antibodies: A Laboratory Manual,* Cold Spring Harbor Laboratory Press (1990); Harlow and Lane, *Using Antibodies: A Laboratory Manual,* Cold Spring Harbor Laboratory Press (1999); Crawley et al., *Current Protocols in Neuroscience,* John Wiley and Sons (1997, and Supplements to 2001); and Kleitman et al., *Culturing Nerve Cells,* pp. 337-378, MIT Press, Cambridge, Mass./London, England, G. Banker and K. Goslin, Eds. (1991); each of which is incorporated herein by reference in its entirety.

Enzymatic reactions and cell culture and purification techniques are performed according to manufacturer's specifications, as commonly accomplished in the art, or as described herein. The nomenclature used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Throughout this specification and these claims, the word "comprise" or variations such as "comprises" or "comprising" will be understood to imply the inclusion of a stated element or group of elements but not the exclusion of any other element or group of elements.

All publications, patents and other documents mentioned herein are incorporated by reference in their entirety.

In order to further define the invention, the following terms and definitions, unless otherwise indicated, shall be understood to have the following meanings:

The term "polypeptide" encompasses native or artificial proteins, protein fragments, and polypeptide analogs of a protein sequence. As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), incorporated herein by reference. When the amino acids are alpha-amino acids, either the L-optical isomer or the D-optical isomer can be used. A polypeptide encompasses an amino acid sequence and includes modified sequences such as glycoproteins, D-amino acid modified polypeptides, and the like. In addition, use of amino acid analogs is contemplated. Examples of amino acid analogs include, but are not limited to, ethyl esters, methyl esters, naphthylamides, and 7-amido-4-methyl coumarin. A polypeptide may be monomeric or polymeric. In certain embodiments, a polypeptide, whether monomeric or polymeric, comprises at least five, six, seven, eight or more amino acids.

In some embodiments, retro-inverso peptides are used. "Retro-inverso" means an amino-carboxy inversion as well as enantiomeric change in one or more amino acids (i.e., levantory (L) to dextrorotary (D)). A polypeptide of the disclosure encompasses, for example, amino-carboxy inversions of the amino acid sequence, amino-carboxy inversions containing one or more D-amino acids, and non-inverted sequence containing one or more D-amino acids. Retro-inverso peptidomimetics that are stable and retain bioactivity can be prepared as described by Brugidou et al. (*Biochem. Biophys. Res. Comm.* 214(2): 685-693 (1995)) and Chorev et al. (*Trends Biotechnol.* 13(10): 438-445 (1995)).

The term "isolated protein" or "isolated polypeptide" refers to a protein or polypeptide that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% w/w of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification and quantification.

The term "SLPI-derived" polypeptide, polypeptide fragment or PTD as used herein refers to a molecule that is derived (physically or by design) from a native SLPI, or a mutant SLPI derivative as described in the art (see supra; see PCT/US2007/008279 filed Mar. 30, 2007) and which comprises part but not all of the amino acid residues that comprise full length, native or mutant derivative SLPI. As used herein, the term "SLPI-derived PTD" refers to a protein translocation domain comprising amino acid sequences derived (physically or by design) from a native or mutant SLPI full length protein.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long. The term "functional fragment" refers to fragments of a polypeptide that retain an activity of the polypeptide. For example, a functional fragment of a PTD comprises a fragment which retains transduction activity.

Polypeptides and fragments can have the same or substantially the same amino acid sequence as the naturally occurring protein. "Substantially identical" means that an amino acid sequence is largely, but not entirely, the same, but retains a functional activity of the sequence to which it is related. An example of a functional activity is transduction activity.

In general two amino acid sequences are "substantially identical" if they are at least about 85%, preferably at least about 90%, and more preferably at least about 95%, 96%, 97%, 98% or 99% or more identical, or if sequence variations consist of conservative amino acid substitutions. Conservative substitutions are defined as the exchange of one amino acid for another having similar properties. Examples of conservative substitutions include, but are not limited to 1) glycine and alanine; 2) valine, isoleucine, and leucine; 3) aspartic acid and glutamic acid; 4) lysine and arginine; 5) asparagine and glutamine; and 6) serine and threonine. A computer program, such as the BLAST program (Altschul et al., 1990) can be used to compare sequence identity.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), incorporated herein by reference.

The term "polynucleotide" refers to a polymeric form of nucleotides of at least 10 bases in length, either ribonucleotides or deoxynucleotides or a modified form of either type of nucleotide. The term includes single and double stranded forms. A reference to a nucleotide sequence encompasses its complement unless otherwise specified. Thus, a reference to a nucleic acid having a particular sequence should be understood to encompass its complementary strand, with its complementary sequence.

The term "isolated polynucleotide" refers to a polynucleotide of genomic, cDNA, or synthetic origin or some combination thereof, which by virtue of its origin: (1) is not associated with all or a portion of polynucleotides with which the "isolated polynucleotide" is found in nature, (2) is operably linked to a polynucleotide to which it is not linked in nature, or (3) does not occur in nature as part of a larger sequence.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection or purification, if desired.

"Operably linked" sequences are sequences that can be expressed together from the same expression control sequences, and/or used together to express a product of interest. Operably linked sequences include both expression control sequences that are contiguous with the gene of interest and expression control sequences that act in trans or at a distance to control the gene of interest. A nucleic acid encoding a SLPI-derived PTD may be operably linked to a nucleic acid encoding a cargo moiety in such a way that a fusion between the PTD and cargo moiety results upon expression in a host cell.

The term "expression control sequence" as used herein means polynucleotide sequences that are necessary to effect the expression and processing of coding sequences to which they are ligated or otherwise operably attached. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector," as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As used herein, the terms "label" or "labeled" refers to incorporation of another molecule in a polypeptide of the invention. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "PTD" refers to a protein transduction domain, which is a Polypeptide sequence that is able to translocate across one or more biological membranes. The term "SLPI-derived PTD" refers to a protein transduction domain that comprises part of the amino acid sequence of secretory leukocyte protease inhibitor. A SLPI-derived PTD is able to translocate into at least 50%, 60%, 70%, 80%, 90% or preferably 95%, 96%, 97%, 98%, 99% or 100% of cell types to which it is applied. Further, a SLPI-derived PTD is able to translocate into at least 50%, 60%, 70%, 80%, 90% or preferably 95%, 96%, 97%, 98%, 99% or 100% of a population of cells to which it is applied.

The term "cargo moiety" includes, but is not limited to, proteins, lipids, nucleic acids, carbohydrates and small molecules and other chemical compounds.

As used herein, the phrase "therapeutically-effective amount" means an amount of a substance comprising a SLPI-derived PTD of the invention such that the subject exhibits a therapeutic effect after being treated under the selected administration regime (e.g., the selected dosage levels and times of treatment).

The term "treating" is defined as administering, to a subject, a therapeutically-effective amount of a compound of the invention, to prevent the occurrence of symptoms, to control or eliminate symptoms, or to palliate symptoms associated with a condition, disease, or disorder associated with neuronal death or lack of neuronal growth.

The term "subject," as described herein, is defined as a mammal or a cell in culture. In a preferred embodiment, a subject is a human or other animal patient in need of treatment.

The term "patient" includes human and veterinary subjects.

SLPI-Derived PTDs and Uses Thereof

A SLPI-derived PTD of the invention may comprise any fragment or combination of fragments of the SLPI polypeptide (SEQ ID NO: 1), wherein the SLPI-derived PTD has the ability to translocate across one or more biological membranes. In one embodiment, the SLPI-derived PTD is able to translocate across at least the outer cell membrane or membranes of a host cell (prokaryotic or eukaryotic). In another embodiment, the SLPI-derived PTD is able to translocate across at least the nuclear membrane of a eukaryotic host cell. In a preferred embodiment, the SLPI-derived PTD is able to translocate across at least both the outer cell membrane(s) and the nuclear membrane.

In one embodiment, a SLPI-derived PTD may comprise, for example, amino acids 11-25 (sequence PPKKSAQCLRYKKPE) (SEQ ID NO: 2), or a functional fragment thereof. In another embodiment, a SLPI-derived PTD may consist or consist essentially of amino acids 11-25 (sequence PPKKSAQCLRYKKPE) (SEQ ID NO: 2) of the SLPI protein, or a functional fragment thereof. In another embodiment, a SLPI-derived PTD may comprise or consist essentially of, for example, amino acids 49-63 (sequence DPVDTPNPTRRKPGK) (SEQ ID NO: 3) of the SLPI protein, or a functional fragment thereof. A SLPI-derived PTD may also comprise or consist essentially of a larger fragment of the SLPI protein; for example, amino acids 1-54 (SEQ ID NO: 4), amino acids 55-107 (SEQ ID NO: 5), or amino acids 58-107 (SEQ ID NO: 6), as described in Masuda et al. (*Brit. J. Pharm.* 115:883-888 (1995)) and Mitsuhashi et al. (*J. Pharm. Exp. Ther.* 282:1005-1010 (1997)).

In another embodiment, a SLPI-derived PTD may comprise or consist essentially of a protein transduction domain that is 50%, 60%, 70%, preferably 80%, 90%, or most preferably 95%, 96%, 97%, 98%, or 99% identical to: (a) SEQ ID NO: 2 or a functional fragment thereof; or (b) SEQ ID NO: 3 or a functional fragment thereof. Amino acid substitutions in these sequences may be made, for example, to enhance protein stability.

In another embodiment, a SLPI-derived PTD may comprise or consist essentially of a chimeric protein transduction domain, wherein the chimeric PTD comprises one or more fragments from each of two different SLPI-derived PTDs, or from at least one SLPI-derived PTD and at least one non-SLPI-derived PTD, which may be a naturally derived PTD from, for example, AntHD, VP22, or TAT; an artificial PTD; or a PTD selected from a random library.

In certain embodiments, the invention provides a transduction complex comprising (1) at least one SLPI-derived PTD, and (2) at least one cargo moiety. The cargo moiety may comprise or consist essentially of, for example, (1) one or more polypeptides or fragments thereof; (2) one or more polynucleotides or oligonucleotides (e.g., ribozymes, antisense molecules, shRNAs, miRNAs or other polynucleotides that mediate RNA interference or RNA regulation); and/or (3) one or more small molecules, drugs or other compounds that are capable of being linked or fused to a SLPI-derived PTD. The complex of the invention may thus comprise one or more SLPI-derived PTD linked to one or more agents that provide, for example, an effect that serves at least one therapeutic, diagnostic, or research purpose (or any combination thereof) when delivered to a targeted cell.

In certain embodiments, the transduction complex comprises or consists essentially of at least two SLPI-derived PTDs. The transduction complex may comprise or consist of, e.g., three, four, five, six, seven, eight, nine, or ten or more SLPI-derived PTDs. Studies have indicated that inclusion of more than one PTD in a transduction complex may increase transduction efficiency (see, e.g., U.S. Patent Application No. 2003/0125242).

In other embodiments, a polypeptide comprising one or more SLPI-derived PTDs is optionally modified to include a targeting signal or domain. The targeting signal or sequence can be specific for a tissue, organ, cell, organelle, non-nuclear organelle, or cellular compartment. Thus, the polypeptides, complexes, and compositions disclosed herein can be targeted to specific intracellular regions, compartments, or organelles. In one embodiment, the SLPI-derived PTD is modified to include a nuclear localization signal (NLS). In another embodiment, the SLPI-derived PTD is modified to include a nuclear export signal (NES) or a cytoplasmic localization signal (CLS).

To target a polypeptide, complex, or composition to one or more particular cell types, signal peptides can be selected from the SIGPEP database (von Heijne, Protein Sequence Data Analysis 1:4142 (1987); von Heijne and Abrahmsen, L., FEBS Letters 224:439-446 (1989)). Algorithms can also predict signal peptide sequences (see, e.g., SIGFIND—Signal Peptide Prediction Server version SignalP V2.0b2, accessible at world wide web sites cbs.dtu.dk/services/SignalP-2.0/or world wide web 139.91.72.10/sigfind/sigfind.html). When a specific cell type is to be targeted, a signal peptide used by that cell type can be chosen. For example, signal peptides encoded by a particular oncogene can be selected for use in targeting cells in which the oncogene is expressed. Additionally, signal peptides endogenous to the cell type can be chosen for importing biologically active molecules into that cell type. Methods for testing the ability of a signal peptide to translocate across the cell membrane of a given cell type are known in the art (see, e.g., U.S. Pat. No. 5,807,746).

In some embodiments, translocation activity of the SLPI-derived PTD is controlled by the presence of an inhibitor of the SLPI-derived PTD that reduces its translocation characteristics. Modification of the polypeptide, complex, or composition by cleavage may release the inhibiting component, allowing translocation of the polypeptide, complex, or composition into the cell. This may permit, for example, translocation of compounds into cells uniquely or preferentially expressing an extracellular protease while limiting entry into cells not expressing said protease.

In some embodiments, a SLPI-derived PTD of the invention, optionally linked or fused to one or more cargo moieties, is able to translocate across a cell membrane within less than 60, 45, 30, 20, or 15 minutes, preferably less than 10 minutes, and most preferably less than 5 minutes of application to a target cell. In some embodiments, the SLPI-derived PTD or transduction complex is able to translocate across a nuclear membrane within less than 60, 45, or 30 minutes, preferably less than 20, 15, or 10 minutes, and most preferably less than 5 minutes of application to a target cell.

Cargo Moieties

The invention provides a transduction complex which comprises (1) at least one SLPI-derived PTD, and (2) at least one cargo moiety that is capable of being linked or fused to a SLPI-derived PTD. A cargo moiety may comprise, for example, (1) one or more polypeptides or fragments thereof; (2) one or more polynucleotides (e.g., ribozymes, antisense molecules, siRNAs, miRNAs, shRNAs and other polynucleotides or oligonucleotides); and/or (3) one or more small molecules, drugs, or compounds.

In one embodiment, the transduction complex comprises one or more polypeptides. Such polypeptides may be active or inactive forms of proteins, and may be activated upon cleavage at specific sites, for example, upon introduction to a targeted intracellular compartment. In one embodiment, the polypeptides may comprise, e.g., agents that provide at least one therapeutic effect to the targeted cell, tissue, and/or subject. In another embodiment, the polypeptides may comprise toxins that cause cell death or impair cell survival when introduced into a cell, such as, for example, campylobacter toxin, diptheria toxin, cholera toxin, pertussis toxin, pierisin, or nigrin. In another embodiment, the polypeptides may comprise, e.g., detectable enzymes or other reporter proteins, such as, for example, GFP, luciferase, β-galactosidase, and alkaline phosphatase.

In yet another embodiment, the polypeptides may comprise protein domains that interact with other biological molecules, including other proteins, nucleic acids, lipids, etc. These protein domains frequently act to provide regions that induce formation of specific multiprotein complexes for recruiting and confining proteins to appropriate cellular locations, or affect specificity of interaction with target ligands. Examples of protein domains include, but are not limited to: SH2 domain (src homology domain 2), SH3 domain (src homology domain 3), PTB domain (phosphotyrosine binding domain), FHA domain (forkedhead associated domain), WW domain, 14-3-3 domain, pleckstrin homology domain, C1 domain, C2 domain, FYVE domain (Fab-1, YGL023, Vps27, and EEA1), death domain, death effector domain, caspase recruitment domain, Bcl-2 homology domain, bromo domain, chromatin organization modifier domain, F box domain, hect domain, ring domain (Zn+2 finger binding domain), PDZ domain (PSD-95, discs large, and zona occludens domain), sterile a motif domain, ankyrin domain, arm domain (armadillo repeat motif), WD 40 domain and EF-hand (calretinin), PUB domain (Suzuki et al., Biochem. Biophys. Res. Commun. 287: 1083-87 (2001)), nucleotide binding domain, Y Box binding domain, H.G. domain, all of which are well known in the art. Because protein interaction domains play an important role in cellular regulation, introduction of protein interaction domains that act in a specific regulatory pathway may allow for activation or inactivation of such pathways in normal and diseased cells.

Additionally or alternatively, the transduction complex may comprise one or more polynucleotides. Upon translocation into the cell, these polynucleotides may be introduced into the genetic material of the host and/or be translated into polypeptides. In one embodiment, the polynucleotides encode, e.g., agents that provide at least one therapeutic effect to the targeted cell, tissue, and/or subject.

In another aspect, the polynucleotides may comprise decoy oligonucleotides. Such decoys "compete" with consensus sequences in target genes for binding of one or more proteins (e.g., transcription factors or other nucleic acid binding proteins). If delivered into the cell in sufficient concentrations, these "decoys" have the potential to attenuate the binding of the nucleic acid binding protein and may thus attenuate the ability of the protein to regulate the expression of its target gene(s) (see, e.g., Mann and Dzau, J Clin. Invest. 106(9): 1071-5 (2000)).

In another aspect, the polynucleotides may comprise RNAs capable of inducing RNA interference or RNA silencing, such as RNAi, interfering RNA, or dsRNA (Bosher et al.,

*Nat. Cell Biol.* 2: E31-36 (2000); Zamore et. al., *Cell* 101: 25-33 (1997)). These and other small regulatory RNAs provide a basis for silencing expression of genes, thus permitting a method for altering the phenotype of cells. The RNAs may comprise modified and synthetic RNA made by known chemical synthetic methods and/or by in vitro transcription of nucleic acid templates carrying promoters (e.g., T7 or SP6 promoters; and other class II or class III promoters).

In another aspect, the polynucleotides may constitute part of a ribozyme or DNAzyme. Ribozymes and DNAzymes are nucleic acids capable of catalyzing cleavage of target nucleic acids in a sequence specific manner. As with antisense nucleic acids, nucleic acids catalyzing cleavage of target nucleic acids may be directed to a variety of expressed nucleic acids, including those of cellular genes or pathogenic organisms. Conjugation of a PTD to a ribozyme is described in Villa et al., *FEBS Letters* 473(2):241-248 (2000).

Additionally or alternatively, the transduction complex may comprise one or more small molecules, drugs, small molecules or other chemical compounds. A wide variety of compounds of interest, including, for example, bioactive compounds, fluorochromes, dyes, metals and metal chelates may be delivered into the cell using SLPI-derived PTDs.

In one embodiment, the small molecules comprise reporter compounds, such as fluorescent, phosphorescent, and radioactive labels, and detectable ligands. Useful fluorescent compounds include, for example, fluorescein, rhodamine, TRITC, coumadin, Cy5, ethidium bromide, DAPI, and the like. Suitable fluorescent compounds are described in Haughland, R. P., *Handbook of Fluorescent Probes and Research Chemicals*, 9th Ed., Molecular Probes, Oregon. (2003); incorporated herein by reference). Radioactive compounds can be used either for signaling purposes or to provide a therapeutic effect by specific delivery to a targeted cell (e.g., in the form of radiopharmaceutical preparations). Radioactive nuclides include, for example, $^3H$, $^{14}C$, $^{32}P$, $^{35}S$, $^{51}Cr$, $^{57}Co$, $^{59}Fe$, $^{67}Ga$, $^{82}Rb$, $^{89}SR$, $^{99}Tc$, $^{111}In$, $^{123}I$, $^{125}I$, $^{129}I$, $^{131}I$, and $^{186}Re$.

In another embodiment, the small organic molecules are chelating ligands, or macrocyclic organic chelating molecules, for example, metal chelating compounds used to image intracellular ion concentrations or used as contrast agents for medical imaging purposes. Metal chelating compounds may also be used for therapy; for example, radioactive metals may deliver small doses of radiation to a specific site in the body.

Other compounds suitable for PTD-mediated delivery include, for example, drugs such as chemotherapeutic compounds, including by way of example and not limitation, vinblastine, bleomycin, taxol, cis-platin, adriamycin, mitomycin, daunorubicin, and doxorubicin, and other antitumor agents such as the endiyne family of antibiotics. Inclusion of a nuclear localization signal further targets these compounds to the cell nucleus, where these antineoplastic agents typically function. In another embodiment, the compounds are small molecule modulators of telomerase activity, such as, for example, alterperynol, isothiazolone derivatives, rhodacyanine derivatives, rubromycin derivatives, diazaphilonic acid, and others known in the art.

PTD-Cargo Moiety Complexing

A cargo moiety can be complexed to a SLPI-derived PTD by any method known in the art and which is appropriate for a particular cargo moiety, providing that functionality of either the SLPI-derived PTD or the cargo moiety is not destroyed. The skilled artisan will be able to choose the appropriate method to complex a cargo moiety with a PTD. Examples of such methods include, but are not limited to, chemical cross-linking with either a homobifunctional or heterobifunctional cross-linker, which may include a cleavage site; genetic fusion by, for example, linking a coding sequence for a SLPI-derived PTD in-frame with a coding sequence for a polypeptide cargo moiety, wherein a cleavage site may be introduced between the two; and use of bridging molecules such as, for example, (a) streptavidin and biotin, (b) glutathione and glutathione-S-transferase, and (c) polyhistidine and an affinity chromatography reagent. These methods are well known in the art.

A polynucleotide may be linked to a SLPI-derived PTD by, for example, providing a cargo moiety that comprises a DNA/RNA binding protein that binds selectively to a DNA/RNA binding sequence of the desired polynucleotide.

A skilled artisan will be able to determine if the respective parts of the transduction complex retain biological activity. The PTD retains biological activity if it can transport cargo across one or more biological membranes, e.g., a cell membrane and/or a nuclear membrane. Transport activity can be ascertained, for example, by adding the PTD cargo moiety complex to cells and assaying the cells to determine whether the cargo moiety was delivered across the biological membrane. One skilled in the art can determine if the cargo is located intracellularly or within the nucleus using methods well known in the art (e.g., immunohistochemical staining). The cargo moiety can be assayed for activity using a method acceptable for the type of cargo moiety (e.g., an enzyme assay for an enzyme, a transformation assay for an oncoprotein, an anti-apoptotic assay for an anti-apoptosis protein, and an immortalization assay for an immortalization protein). These assays are well known in the art and are described, e.g., in Sambrook et al., 1989 and Ausubel et al., 1989.

Target Cells

"Target" cells include any cell targeted for delivery of the transduction complex of the invention. SLPI-derived PTDs of the invention may transport one or more cargo moieties into a variety of cells, prokaryotic or eukaryotic. Exemplary eukaryotic target cells include mammalian, amphibian, reptilian, avian, plant and insect cells. Cells can be primary cells or cell lines.

Mammalian cells can be, e.g., human, monkey, rat, mouse, dog, cow, pig, horse, hamster, and rabbit cells. Primary cells from mammals include, but are not limited to, adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, ovary cells, pancreatic beta cells, renal cells, smooth muscle cells, and striated muscle cells. Examples of amphibian cells include, but are not limited to, frog and salamander. Reptilian cells include, but are not limited to, snake and lizard cells. Examples of avian cells include, but are not limited to, chicken, quail, and duck cells. Plant cells include but are not limited to alfalfa, *Arabidopsis*, barley, *Brassica*, broccoli, canola, cabbage, citrus, corn, cotton, garlic, hemp, oat, oilseed rape, onion, canola, flax, maize, pea, peanut, pepper, potato, rice, rye, sorghum, soybean, strawberry, sugarcane, sugarbeet, tomato, poplar, potato, pine, fir, eucalyptus, apple, lettuce, peas, lentils, grape, banana, tea, turf grasses, etc., as well as other edible or fruit bearing plants, ornamentals and experimental plant cells lines. Insect cells can be, for example, *Drosophila* and *Lepidoptera* cells. Cell lines include, but are not limited to, 182-PF-SK, 184A1, 2H-11, 2F-2B, 293, 27FR, 28SC, 3B-11, 4T1, 7F2, A172, A375.S2, A-253, A-431, ARH-77, AHH-1, AML-193, A-10, BS-C-1, BHK-21, BE(2)-117, BCE, BJ, B16-F0, BT-20, BT-474, BLP-1, BRL-3A, BLO-11, CTX-TNA2, C8-D30, C8-S, CPAE, CPA47, CHO-K1, CV-1, C6, CHP-212, C8-B4, C166, C-211, CCD-25Sk, C32, CTPS, C1-S1, C127, CF41-Mg, CMMT, CAMA-1, C5/MJ, C3A, C2C12, COS-1, COS-7, Dempsey, Detroit 532, Daudi, EBTr(NBL-4), EOMA, EJG, E Derm, EB, EM-9, FBHE, FL, F98, G-361, GK-5, GDM-1, G-7, G-8, HIG-82, H9c2(2-1), HUV-EC-C, HeLa, HaK, HEp-2, HT-1080, HG-261, HEL-299, H2.35, HEp-G2, H4, HAAE-1, HAAE-2, HUVE-12, Hs27, Hs68, HL-60, H4TG, Hepa1-6, IMR-32, IP-1B, J1-31, J2 3T3, JC, JHK3, KB, K-562, KG-1, L-132, LLC-MK2, LA7, LMH, L8, MDBK, M059K, Mar Vin, MM5MTC, $MCF_7$, MoB, MOLT-3, MH1Cl, NIH 3T3, Neuro-2a, NB41A3, NIE-115, NMVMG, NMU, OV-90, P19, PFSK-1, PC-12, PaCa-2, PANC-1, QM-7, RF/6A, RK13, rat1, rat2, RG2, RT101, RBA, Rn2T, RBL-1, Swiss SFMF, SK-N-AS, SH-SY5Y, Sf1Ep, SW-13, SW-527, SK-BR-3, SNU449, SK-Hep1, Snyder, Sf9, Sf21, T98G, TH-1, Toledo, UV41, Vero, WS6, WR-21, XP17BE, Y-1, ZR-75-1, and ZR-75-30.

In comparison to certain other PTDs, SLPI and its derivatives appear to be preferentially internalized by neurons (See Example 5). Accordingly, in one embodiment, the target cells are neurons. In an exemplary embodiment, the target cells are neurons in the optic system, e.g., cells in the retinal ganglion cell layer (See Example 6).

Nucleic Acids

The invention provides an isolated nucleic acid molecule encoding a polypeptide that comprises one or more SLPI-derived PTDs of the invention. In one embodiment, the invention provides an isolated nucleic acid molecule that additionally encodes one or more polypeptide cargo moieties linked to the one or more SLPI-derived PTDs. Further, the isolated nucleic acid molecule may encode a linker polypeptide joining the SLPI-derived PTD(s) and the cargo polypeptide(s). This linker polypeptide may optionally contain, for example, cleavage site(s) such that the SLPI-derived PTD(s) can be cleaved from the cargo polypeptide(s) after delivery to the targeted intracellular compartment. The polypeptide cargo moiety can be complexed to either the amino terminus of the PTD or to the carboxy-terminus of the PTD. Alternatively or additionally, the polypeptide cargo moiety can be complexed to an internal residue of the PTD, e.g., by complexing to an internal side chain residue of the PTD directly or indirectly via a linking group, using methods available to the skilled worker.

The invention also provides a recombinant expression vector comprising an isolated nucleic acid molecule of the invention. The recombinant expression vector may be operably linked to an expression control sequence, which may, for example, comprise a promoter or enhancer that is specific to cells, tissues, or organs to which the vector is transduced. The vector preferably includes tag sequence(s), such as a series of Histidine, Hemaglutinin, Myc, or Maltose binding protein codons, for example, in order to facilitate purification of the vector. Further, a fusion partner such as lysine RNA polymerase may be introduced into the vector to increase solubility. One or more glycine and/or spacer amino acids may be incorporated to increase flexibility and stability of the fusion protein encoded by the vector. The vector may also comprise a cleavage site, which may be recognized by a protease specifically present in a certain intracellular compartment. This cleavage site may be used to separate the SLPI-derived PTD and the cargo moiety, or to cleave another part of the fusion protein.

The invention also provides transformed cells and cell lines comprising the expression vector of the invention. Also provided are transgenic animals that produce one or more SLPI-derived PTDs of the invention and optionally one or more cargo polypeptides linked to the one or more SLPI-derived PTDs. A transgenic plant or non-human animal comprising an isolated polynucleotide or polypeptide of the invention is included.

Methods of Use for SLPI-derived PTDs

Another embodiment of the invention provides a method of delivering a cargo moiety to an intracellular compartment of a cell using a SLPI-derived PTD. A cell is contacted in vitro or in vivo with a transduction complex comprising one or more SLPI-derived PTDs linked to one or more cargo moieties, thereby delivering the one or more cargo moieties to an intracellular compartment of the cell, such as the cytoplasm, nucleus, or an intraorganelle compartment. In a preferred embodiment, the intracellular compartment is the nucleus. The cargo moiety may be a therapeutic agent, a diagnostic agent, a research reagent (e.g., enzyme, cofactor, ligand, receptor or the like) or a combination of any of the foregoing.

In one embodiment, a lysosomotrophic agent is used to enhance the structural and functional safety of the transduction complex during translocation into an intracellular compartment. The lysosomotrophic agent may be selected from a group consisting of, for example, chloroquine, monensin, amantadine, and methylamine. Many other such agents are known in the art and may be similarly used to protect or enhance the bioactivity of the transduction complex.

The data presented in the Examples herein provide the first evidence that SLPI can rapidly accumulate in the nuclei of neurons, which suggests that SLPI contains a protein transduction domain similar to those described for the Antennapedia and HIV-Tat proteins. We further show herein that a peptide derived from amino acids 11-25 of the SLPI protein can localize to the nuclei of neurons in a similar manner. The internalization of SLPI and its related peptide is observed even when neurons are exposed to low temperatures, which indicates that the internalization of SLPI does not require energy from the cell. This means that SLPI can enter a target cell virtually unimpeded. Most importantly, we have observed that SLPI is internalized by neurons in the retina when it is injected into the eye. These experiments demonstrate that SLPI is capable of entering cells when administered to live animals. These findings have tremendous implications for drug design and delivery.

Therapeutic Uses for SLPI-Derived PTDs

Therapeutic agents may be conjugated to a SLPI-derived peptide, which in turn will greatly facilitate their entry into cells. It appears, moreover, that SLPI is preferentially internalized by neurons, and so, it is expected that the SLPI-derived peptide may be particularly effective as a means for delivering treatments for neurological disorders. Because SLPI localizes specifically to the nucleus, it is also possible that a SLPI-derived peptide may be useful for delivery of agents that mediate gene therapy. Nucleic acid containing agents, including those that repress or express a gene of interest, may be linked to a SLPI-derived peptide and thereby be delivered specifically to the nuclei of the target cells, where the nucleic acid will be expressed or otherwise perform its desired function. Ultimately, the cell-penetrating properties of SLPI may be useful as a basis for treating a wide range of human diseases, including neurological disorders, cancers and genetic deficiencies.

Thus, in certain embodiments, the transduction complex of the invention comprises one or more SLPI-derived PTDs linked to one or more cargo moieties that provide at least one therapeutic effect when delivered to a targeted cell. A therapeutic effect may comprise, for example, preventing the occurrence of symptoms, controlling or eliminating symptoms, or palliating symptoms associated with a condition, disease or disorder. The therapeutic effect may also comprise protection against the condition, disease or disorder. The term "therapeutic" is used in a generic sense and includes treating agents, prophylactic agents, and replacement agents. Cargo moieties that provide at least one therapeutic effect may comprise, for example, cell cycle control agents; agents which inhibit cyclin proteins, such as antisense polynucleotides to the cyclin G1 and cyclin D1 genes; growth factors such as, for example, epidermal growth factor (EGF), vascular endothelial growth factor (VEGF), erythropoietin, G-CSF, GM-CSF, TGF-α, TGF-β, and fibroblast growth factor; cytokines, including, but not limited to, Interleukins 1 through 13 and tumor necrosis factors; anticoagulants, anti-platelet agents; anti-inflammatory agents; tumor suppressor proteins; clotting factors including Factor VIII and Factor IX, protein S, protein C, antithrombin III, von Willebrand Factor, cystic fibrosis transmembrane conductance regulator (CFTR), DNA or RNA vaccines, and antigens specific to a pathogen selected from the group consisting of viruses, bacteria, mold, and various cancer cells.

In one embodiment, a cargo moiety fused to a SLPI-derived PTD can be a negative selective marker or "suicide" protein, such as, for example, the Herpes Simplex Virus thymidine kinase (TK). Targeting such a transduction complex to undesired cells (e.g., tumor cells or virally infected cells) may cause inhibition, suppression, or destruction of said cells upon translocation of the complex and expression of the suicide protein.

In another embodiment, a 'Trojan Horse' strategy can be used to treat infectious disease (see, e.g., Vocero-Akbani et al., *Nat. Med.* 5, 29-33 (1999)). For example, the HIV protease present in HIV-infected cells may be used to activate a killing molecule such as a SLPI-derived PTD—caspase-3 pro-apoptotic zymogen fusion protein, wherein the fusion protein substitutes HIV proteolytic cleavage sites for endogenous caspase cleavage sites. Upon translocation into HIV-infected cells, the pro-caspase-3 is selectively processed into an active protease, resulting in cell death specifically targeted to HIV-infected cells. A similar approach may be used for preventing other infectious diseases such as hepatitis C, cytomegalovirus, malaria, and other diseases providing pathogen-encoded proteases.

In one embodiment, the transduction complex is used in the treatment of diseases such as, for example, cancer; heart diseases such as myocardial infarction; diabetes; cystic fibrosis; Canavan disease; hypercholesteremia; anemia; atherosclerosis; muscular dystrophy; AIDS; asthma; arthritis; adenosine deaminase deficiency; haemoglobinopathies such as sickle cell anaemia and the thalassemias; lysosomal storage diseases (LSDs) such as infantile or late infantile ceroid lipofuscinoses, Gaucher, Juvenile Batten, Fabry, MLD, Sanfilippo A, Late Infantile Batten, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III, or Sandhoff disease; neurodegenerative diseases such as Huntington's disease, Parkinson's disease, ALS, hereditary spastic hemiplegia, primary lateral sclerosis, multiple sclerosis, spinal muscular atrophy, Kennedy's disease, Alzheimer's disease, and polyglutamine repeat diseases; autoimmune diseases; infectious diseases; opthalmological diseases such as optic neuritis, diabetic retinopathy, macular degeneration, and glaucoma; and all genetic disorders In a preferred embodiment, the transduction complex is used to treat opthalmological diseases such as, for example, multiple sclerosis, optic neuritis, diabetic retinopathy, macular degeneration, and glaucoma.

In one embodiment, a transduction complex comprising one or more SLPI-derived PTDs is used for gene therapy. "Gene therapy" includes both conventional gene therapy where a lasting effect is achieved by a single treatment, and the administration of gene therapeutic agents, which involves the one time or repeated administration of a therapeutically effective DNA or RNA. The subject may have a genetic disease or an acquired pathology, and the cargo moiety may comprise a heterologous gene encoding a therapeutic agent for treating the disease or pathology. In one embodiment, for example, the subject has a cancer and the cargo moiety comprises a heterologous gene encoding an anti-neoplastic agent.

In one embodiment, the invention provides a composition that comprises a complex comprising one or more SLPI-derived PTDs linked to one or more cargo moieties, or an isolated nucleic acid molecule encoding a polypeptide comprising one or more SLPI-derived PTDs and one or more heterologous polypeptides, and a pharmaceutically acceptable carrier. The composition may also comprise a plurality of the host cells or cell lines of the invention. Compositions of the invention may further comprise one or more other components, such as therapeutic and/or diagnostic agents.

Delivery of the compositions and/or transduction complexes of the invention may take many forms. In one embodiment, a protein delivery method is disclosed. A polypeptide comprising one or more SLPI-derived PTDs, optionally linked to one or more heterologous polypeptides, is purified from the genetically modified host cells or cell lines of the invention. The resulting polypeptide(s) are then optionally linked to other cargo moieties before delivery to a subject.

In another embodiment, a cell graft is used for delivery of fusion polypeptides. The graft comprises a plurality of genetically modified cells attached to a support, which is suitable for implantation into the subject. The support may be formed of a natural or synthetic material.

In yet another embodiment, an encapsulated cell expression system is used for delivery of fusion polypeptides. The encapsulated expression system comprises a plurality of genetically modified cells contained within a capsule, which is suitable for implantation into the subject. The capsule may be formed of a natural or synthetic material. The capsule containing the plurality of genetically modified cells may be implanted in, for example, the peritoneal cavity, the brain or ventricles in the brain, or into the specific disease site.

Pharmaceutical compositions comprising the transduction complex of this invention may be in a variety of forms, which may be selected according to the preferred modes of administration. These include, for example, solid, semi-solid and liquid dosage forms such as tablets, capsules, pills, powders, creams, liquid solutions or suspensions, syrups, suppositories, injectable and infusible solutions, aerosols and the like. The preferred form depends on the intended mode of administration and therapeutic application. Modes of administration may include, but are not limited to, oral, parenteral (including subcutaneous, intravenous, intramuscular, intraarticular, intra-synovial, cisternal, intrathecal, intrahepatic, intralesional and intracranial injection or infusion), topical, rectal, nasal, buccal, vaginal, by inhalation, or by an implanted reservoir, external pump or catheter.

The transduction complexes of this invention may, for example, be placed into sterile, isotonic formulations with or without cofactors which stimulate uptake or stability. The formulation is preferably liquid, or may be lyophilized powder. For example, an agent of the invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see pharmaceutical references, supra). Such pharmaceutically acceptable carriers may include other medicinal agents, carriers, including genetic carriers, adjuvants, excipients, etc., such as human serum albumin or plasma preparations. The compositions are preferably in the form of a unit dose and will usually be administered one or more times a day.

The compositions comprising a compound of this invention will contain from about 0.1 to about 90% by weight of the active compound, and more generally from about 10% to about 30%. The compositions may contain common carriers and excipients, such as corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

For oral administration, the pharmaceutical compositions are in the form of, for example, a tablet, capsule, suspension or liquid. Solid formulations such as tablets and capsules are particularly useful. Sustained release or enterically coated preparations may also be devised. For pediatric and geriatric applications, suspensions, syrups and chewable tablets are especially suitable. The pharmaceutical composition is preferably made in the form of a dosage unit containing a therapeutically-effective amount of the active ingredient. Examples of such dosage units are tablets and capsules.

For therapeutic purposes, the tablets and capsules which can contain, in addition to the active ingredient, conventional carriers such as binding agents, for example, acacia gum, gelatin, methylcellulose, sodium carboxymethylcellulose, polyvinylpyrrolidone (Povidone), hydroxypropyl methylcellulose, sucrose, starch and ethylcellulose sorbitol, or tragacanth; fillers, for example, calcium phosphate, glycine, lactose, maize-starch, sorbitol, or sucrose; lubricants, for example, magnesium stearate, or other metallic stearates, stearic acid, polyethylene glycol, silicone fluid, talc, waxes, oils and silica, colloidal silica or talc; disintegrants, for example, potato starch, flavoring or coloring agents, or acceptable wetting agents.

Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Oral liquid preparations may comprise lipopeptide micelles or monomeric forms of the lipopeptide. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, a water soluble form of the transduction complex can be dissolved in any of the commonly used intravenous fluids and administered by infusion. Intravenous formulations may include carriers, excipients or stabilizers including, without limitation, calcium, human serum albumin, citrate, acetate, calcium chloride, carbonate, and other salts. Intravenous fluids include, without limitation, physiological saline or Ringer's solution. Polyamine and arginase modulators, optionally coupled to other carrier molecules, may also be placed in injectors, cannulae, catheters and lines.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. Lipopeptide micelles may be particularly desirable for parenteral administration. The compounds can be dissolved in polyethylene glycol, propylene glycol, ethanol, corn oil, benzyl alcohol, sodium chloride, and/or various buffers. For intramuscular preparations, a sterile formulation of a polyamine or arginase modulatory agent, or a suitable soluble salt form of the compound, for example a hydrochloride salt, can be dissolved and administered in a pharmaceutical diluent such as Water-for-Injection (WFI), physiological saline or 5% glucose.

Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in microemulsions that are compatible with body tissues.

For topical use, the transduction complex of the present invention can also be prepared in suitable forms to be applied to the skin, or mucus membranes of the nose and throat, and can take the form of creams, ointments, liquid sprays or inhalants, lozenges, or throat paints. Such topical formulations further can include small molecules such as dimethylsulfoxide (DMSO) to facilitate surface penetration of the active ingredient. For topical preparations, a sterile formulation of a transduction complex or suitable salt forms thereof, may be administered in a cream, ointment, spray or other topical dressing. Topical preparations may also be in the form of bandages that have been impregnated with a therapeutic composition.

For application to the eyes, nose or ears, the transduction complex of the present invention can be presented in liquid or semi-liquid form optionally formulated in hydrophobic or hydrophilic bases as ointments, creams, lotions, paints or powders. For rectal or vaginal administration the compounds of the present invention can be administered in the form of suppositories admixed with conventional carriers such as cocoa butter, wax or other glyceride. For aerosol preparations, a sterile formulation of the peptide or lipopeptide or salt form of the compound may be used in inhalers, such as metered dose inhalers, and nebulizers.

Alternatively, the transduction complex of the present invention can be in powder form for reconstitution in the appropriate pharmaceutically acceptable carrier at the time of delivery. In one embodiment, the unit dosage form of the compound can be a solution of the compound or a salt thereof, in a suitable diluent in sterile, hermetically sealed ampules. The concentration of the compound in the unit dosage may vary, e.g. from about 1 percent to about 50 percent, depending on the compound used and its solubility and the dose desired by the physician. If the compositions contain dosage units, each dosage unit preferably contains from 0.1 to 10:mol/kg/hour of the active material. For adult human treatment, the dosage employed preferably ranges from 0.1 to 3.0:mol/kg/hour depending on the route and frequency of administration. For subcutaneous administration, more preferred doses are 0.15-1.5:mol/kg/hour. Doses are administered for at least 24 hours, preferably 48 hours, more preferably 3 days, more preferably 1 week, more preferably 2 weeks, more preferably 3 weeks, 1 month, 2 months or longer. Doses may be administered for periods of up to 3 months, 6 months or 12 months or longer.

The pharmaceutical compositions of this invention may also be administered using microspheres, liposomes, other microparticulate delivery systems or controlled or sustained release formulations placed in, near, or otherwise in communication with affected tissues, the bloodstream, the cerebrospinal fluid, or other locations, including muscle, which enable the targeting of the agent to an affected location in the nervous system. The compositions of the invention can be delivered using controlled (e.g., capsules) or sustained release delivery systems (e.g., bioerodable matrices). Exemplary delayed release delivery systems for drug delivery that are suitable for administration of the compositions of the invention are described in U.S. Pat. Nos. 4,452,775; 5,239,660; and 3,854,480.

Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al., *Biopolymers* 22:547-56 (1985)); poly(2-hydroxyethylmethacrylate) or ethylene vinyl acetate (Langer et al., *J. Biomed. Mater. Res.* 15:167-277 (1981); Langer, *Chem. Tech.* 12:98-105 (1982)).

Liposomes containing transduction complexes can be prepared by well-known methods (see, e.g. DE 3,218,121; Epstein et al., *Proc. Natl. Acad. Sci. U.S.A.* 82:3688-92 (1985); Hwang et al., *Proc. Natl. Acad. Sci. U.S.A.* 77:4030-34 (1980); U.S. Pat. Nos. 4,485,045 and 4,544,545). Ordinarily the liposomes are of the small (about 200-800 Angstroms) unilamellar type in which the lipid content is greater than about 30 mol. % cholesterol. The proportion of cholesterol is selected to control the optimal rate of agent release.

The transduction complexes of this invention may also be attached to liposomes, which may optionally contain other agents to aid in targeting or administration of the compositions to the desired treatment site. Attachment of such agents to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., *J. Cell. Biochem. Abst. Suppl.* 16E 77 (1992)).

Dosages and desired concentrations disclosed herein in pharmaceutical compositions of the present disclosure may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" *In Toxicokinetics and New Drug Development*, Yacobi et al., Eds., Pergamon Press, New York 1989, pp. 42-96.

Kits

One or more SLPI-derived PTDs and one or more cargo moieties can be supplied in a kit. The cargo moiety can be, for example, a small molecule (e.g., a radionuclide, a fluorescent marker, a dye, or a pharmaceutical agent), a protein (e.g., an immortalizing agent, an anti-apoptotic agent, an enzyme, an oncoprotein, a cell cycle regulatory protein, or an antibody), a nucleic acid (e.g., RNA, DNA, and cDNA), or a virus (e.g., papilloma virus, adenovirus, baculovirus, retrovirus core, or Semliki virus core). The PTD and cargo moiety can be supplied in single or divided aliquots, in single or divided containers. Written instructions can be included for assembling a PTD-cargo moiety complex and/or for using the complex. The instructions can be on the label or container. The instructions may simply refer a reader to another location such as a website or other information source.

The invention thus provides the art with reagents, methods, and uses for delivering cargo moieties to an intracellular compartment of a cell using a SLPI-derived PTD.

In order that this invention be more fully understood, the following example are set forth. These examples are for the purpose of illustration only and are not to be construed as limiting the scope of the invention in any way.

EXAMPLES

Example 1

Recombinant SLPI Localizes to the Cytoplasm and Nucleus of Treated Cerebellar Neurons To characterize the transduction abilities of the SLPI protein, cerebellar neurons were isolated from postnatal day 6 (P6) rats (Mukhopadhyay et al., *Neuron* 13:757-767 (1994); DeBellard et al., *Mol. Cell. Neurosci.* 7:89-101 (1996); Cai et al., *Neuron* 22:89-101 (1999)) and treated with 0, 1, 5, and 10 µg/ml recombinant human SLPI (R&D Systems) in SATO culture medium (Doherty et al., *Neuron* 5:209-219 (1990); *Nature* 343:464-466 (1990)). Cells were incubated at 37° C. for 1 hour, and cytoplasmic and nuclear fractions were prepared using NE-PER cytoplasmic and nuclear extraction reagents (Pierce). Protein samples were subjected to SDS-PAGE using 15% SDS polyacrylamide gels and transferred to nitrocellulose. SLPI was detected using a polyclonal antibody to recombinant human SLPI (R&D Systems). SLPI was present in increasing amounts in both the cytoplasmic and nuclear fractions (FIG. 1). The nuclear localization of SLPI was then confirmed by reprobing the membrane for a well-known nuclear marker: phosphorylated cyclic AMP response element binding protein (pCREB; Cell Signaling). As expected, pCREB was only present in the nuclear fractions. Actin was used as a loading control.

Example 2

SLPI Localizes to the Nuclei of Isolated DRG Neurons

Figure 2:
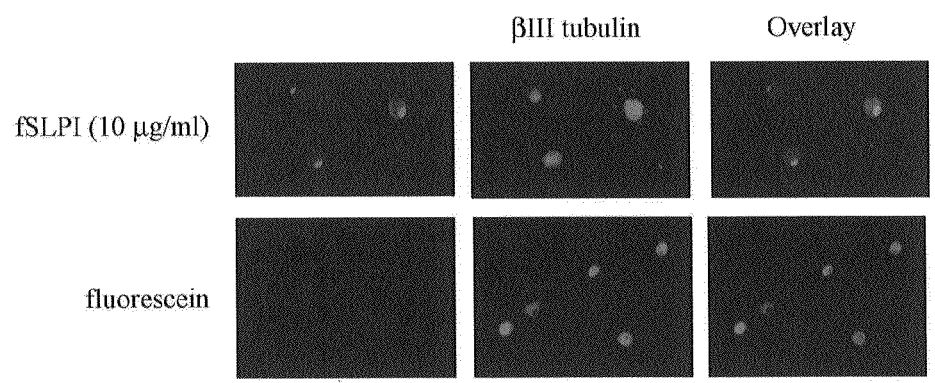
FIG. 2: Internalization of fluorescein-labeled SLPI (fSLPI) by DRG neurons after 1 hour of treatment. In contrast to fluorescein alone, which is not internalized, fSLPI is clearly present in the nuclei of neurons. βIII tubulin is a specific marker for neurons. See Example 2.

To visualize internalization of SLPI in living cells, SLPI was labeled with fluorescein using a Fluorescein-EX protein labeling kit (Molecular Probes). The labeling reaction was performed following the protocol provided by the manufacturer. P5 DRG neurons were isolated (Mukhopadhyay et al., 1994; DeBellard et al., 1996; Cai et al., 1999; supra) and treated with either 10 µg/ml of fluorescein-labeled SLPI (fS-LPI) or unconjugated fluorescein in SATO culture medium. Cells were then plated in 8 well chamber slides coated with 100 µg/ml poly-D-lysine (PDL) and incubated for 1 hour at 37° C. Cells were then fixed with 4% paraformaldehyde and immunostained using a monoclonal antibody to the neuronal marker βIII tubulin (1:1000 dilution, Covance). After an overnight incubation at 4° C., the cells were rinse and incubated successively with biotinylated anti-mouse antibody (1:500 dilution, Amersham) and Texas Red-conjugated streptavidin (1:300 dilution, Amersham). Slides were then coverslipped and viewed using an upright fluorescence microscope. In contrast to fluorescein alone, which was not internalized, fSLPI was clearly present in the nuclei of neurons (FIG. 2).

Example 3

Dose-dependent Internalization of SLPI into Neuronal Nuclei

Figure 3:
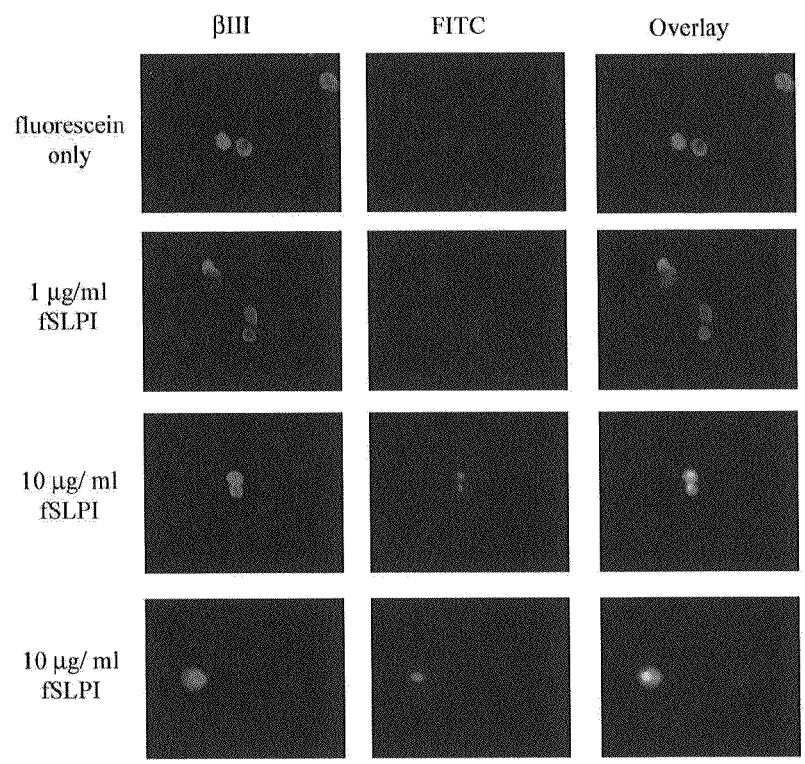
FIG. 3: Internalization of fSLPI by DRG neurons after 5 minutes of treatment. In contrast to fluorescein alone, which is not internalized, fSLPI translocates to nuclei in a dose-dependent manner. βIII tubulin is a specific marker for neurons. FITC is an acronym for fluorescein isothiocyanate, the green fluorophore used in these experiments. See Example 3.

To further characterize SLPI internalization into living cells, P5 DRG neurons in SATO culture medium were treated with unconjugated fluorescein, 1 μg/ml fSLPI, or 10 μg/ml fSLPI and plated onto PDL-coated slides for 5 minutes at 37° C. Cells were then fixed and immunostained for βIII tubulin as described. In contrast to fluorescein alone, which was not internalized, fSLPI was internalized into nuclei within 5 minutes in a dose-dependent manner (FIG. 3).

Example 4

An Exemplary SLPI-derived PTD

Figure 4:
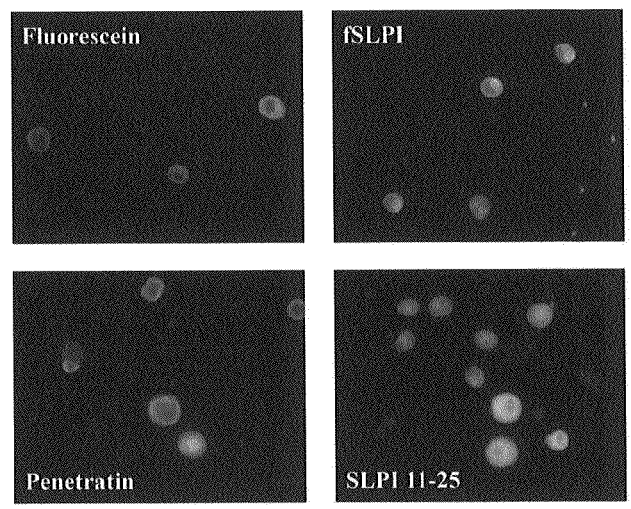
FIG. 4: Internalization of a peptide derived from amino acids 11-25 of human SLPI (SLPI11-25). Unlike fluorescein alone, which is not internalized, fSLPI and SLPI11-25 are both present in the nuclei of DRG neurons after 15 minutes of incubation. Penetratin, a known protein transduction domain peptide, is also present in nuclei. See Example 4.

The transduction characteristics of a SLPI-derived PTD comprising amino acids 11-25 of human SLPI (SLPI11-25) were compared to those of the SLPI protein. SLPI11-25 and penetratin were custom synthesized and labeled with fluorescein at the C-terminus by Invitrogen. P6 DRG neurons were isolated and treated with unconjugated fluorescein, 5 μg/ml fSLPI, 5 μg/ml SLPI11-25, or 5 μg/ml penetratin in SATO culture medium. Cells were plated onto PDL-coated slides and incubated for 15 minutes at 37° C. Cells were then fixed and immunostained for βIII tubulin as described. Unlike fluorescein alone, which was not internalized, fSLPI and SLPI11-25 were both present in the nuclei of DRG neurons after 15 minutes of incubation (FIG. 4). Penetratin, a known protein transduction domain peptide, was also present in nuclei.

Example 5

Internalization of SLPI does not Occur by Endocytosis

To assess whether internalization of SLPI and its derivatives occurs via endocytosis, neurons were treated with penetratin, fSLPI or SLPI11-25 at 4° C., a temperature that normally inhibits endocytic, receptor-based, internalization pathways. For these experiments, monolayers of Chinese hamster ovary (CHO) cells were prepared by plating 75,000 cells into the wells of 8-well chamber slides coated with 20 μg/ml PDL and 10 μg/ml fibronectin (Mukhopadhyay et al., 1994, supra). These cells were incubated overnight at 37° C. to allow the monolayers to form. P6 DRG neurons were then isolated, plated on the monolayers in SATO culture medium, and incubated for an additional 16 hours. This approach was used because of the harsh conditions used in these experiments. Neurons would likely fail to adhere to the slides if plated directly onto PDL and incubated at 4° C., and so, we enhanced adhesion by plating the neurons on CHO cell monolayers and allowing them to extend neurites. Cold SATO culture medium was supplemented with 10 μg/ml penetratin, fSLPI, or SLPI11-25 and added to the wells containing the neurons. The slides were then covered and incubated at 4° C. for 4 hours. Cells were then fixed and immunostained for βIII tubulin as described. Nuclear localization of fSLPI and fSLPI11-25 still occurred at the restrictive temperature, indicating that internalization of SLPI does not occur via endocytosis (FIG. 5).

Figure 5:
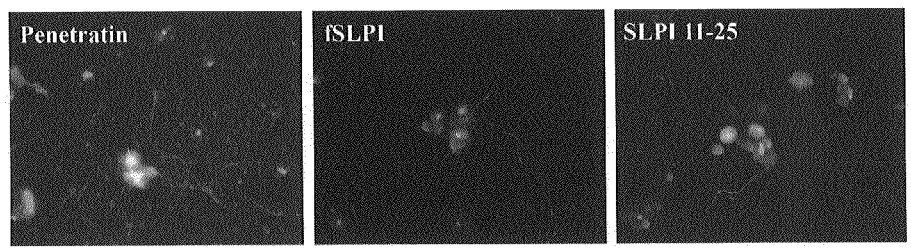
FIG. 5: Nuclear localization of fSLPI and SLPI11-25 still occurs when the cells are incubated at 4° C., indicating that internalization is not occurring via endocytosis. Further, penetratin, but not fSLPI and SLPI11-25, is present in the underlying CHO cell monolayer. This suggests that in comparison to penetratin, SLPI and its derivatives may be preferentially internalized by neurons. See Example 5.

Further, penetratin, but not fSLPI or fSLPI 11-25, was present in the underlying CHO cell monolayer (FIG. 5). This suggests that, in comparison to penetratin, SLPI and its derivatives may be preferentially internalized by neurons.

Example 6

SLPI Injected into Adult Eye Localizes to the Ganglion Cell Layer of the Retina

Figure 6:
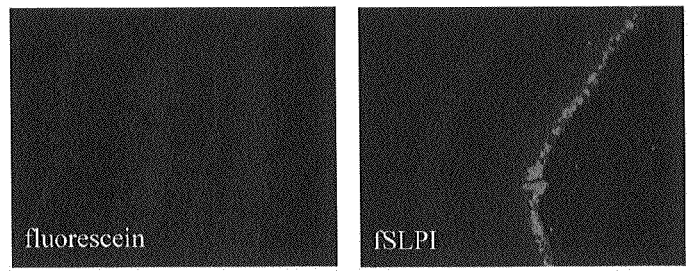
FIG. 6: Internalization of fSLPI in vivo. fSLPI was injected into the eyes of adult rats. The animals were sacrificed after 4 hours. fSLPI is clearly present in the retinal ganglion cell

To analyze the transduction characteristics of SLPI in vivo, fSLPI was injected into the eyes of adult rats. Long-Evans rats (200-250 g) were anesthetized with 2.5% isofluorane and 5 μl of fSLPI (1 μg/μl) or unconjugated fluorescein was injected into the vitreous chamber of the right eye using a glass micropipette (1 μm diameter) attached to a microsyringe pump. 4 hours later, the animals were sacrificed by transcardial perfusion with 4% paraformaldehyde. Following removal of the cornea and lens, the eyes were dissected out and post-fixed in 4% paraformaldehyde for 48 hours. Tissues were then cryoprotected in 30% sucrose in phosphate-buffered saline (PBS) for an additional 48 hours. Tissues were sectioned sagitally at 30 μm on a cryostat and thaw-mounted onto gelatin-coated slides. Slides were rehydrated in PBS, coverslipped, and viewed using an upright fluorescence microscope. fSLPI was clearly present in the retinal ganglion cell layer of the retina at this time point, while no signal was observed with fluorescein alone (FIG. 6). It is envisioned that any of a number of SLPI-derived PTDs will be useful for facilitating entry of diagnostic, therapeutic agents and other cargo moieties into retinal neurons.

Example 7

SLPI Does not Efficiently Cross the Blood Brain Barrier

To assess whether SLPI crosses the blood brain barrier, adult 129SI/SV1MJ mice received intraperitoneal injections of 100 μg fSLPI in sterile PBS or unconjugated fluorescein (500 μl total volume). Mice were sacrificed by transcardial perfusion with 4% paraformaldehyde after 4 and 8 hours. The brains and cervical spinal cords were dissected out and prepared for sectioning as described. Tissues were sectioned coronally at 30 μm and slides were coverslipped as described. No fSLPI was observed in the brain and spinal cord at either time point, suggesting either that SLPI does not cross the blood brain barrier or that SLPI does not reach the blood brain barrier in high enough concentrations to be detected crossing it. Thus, unlike many other known PTDs, SLPI does not appear to cross the blood brain barrier. This may be an inherent property of SLPI or may be secondary to its observed efficient cellular internalization which may in turn prevent SLPI from ever reaching the CNS in high enough concentrations to be detected.

Example 8

A SLPI-derived PTD Injected into Adult Eye

To analyze the transduction characteristics of SLPI11-25 in vivo, fSLPI11-25 is injected into the eyes of adult rats. The animals are sacrificed after 4 hours. fSLPI is expected to be clearly present in the retinal ganglion cell layer of the retina at this time point, while no signal is observed with fluorescein alone.

Example 9

A SLPI-derived PTD and the Blood Brain Barrier

To assess whether SLPI11-25 crosses the blood brain barrier, 129SI/SV1MJ mice received intraperitoneal injections of 100 µg SLPI11-25 or penetratin in sterile PBS (500 µA total volume). Mice were sacrificed after 1 and 4 hours, and the brains and cervical spinal cords were prepared for sectioning as described. Tissues were sectioned coronally at 30 µm and slides were coverslipped as described. No SLPI11-25 was observed in the brain and spinal cord at either time point, suggesting (as in Example 7 for full length SLPI) either that SLPI11-25 does not cross the blood brain barrier or that SLPI11-25 does not reach the blood brain barrier in high enough concentrations to be detected crossing it. Thus, unlike many other known PTDs, SLPI11-25 does not appear to cross the blood brain barrier. This may be an inherent property of SLPI-derived PTDs, or may be secondary to its observed efficient cellular internalization, which may in turn prevent the SLPI-derived PTD from ever reaching the CNS in high enough concentrations to be detected.

Example 10

A SLPI-derived PTD is Expected to Facilitate Entry of a Therapeutic Agent into Retinal Neurons Ranibizumab is a drug used to treat macular degeneration, and is generally administered as an injection into the eye every 4 weeks for 2 years using methods known to those of skill in the art. To facilitate entry of ranibizumab into retinal neurons, SLPI11-25 is fused to ranibizumab as described herein and administered via injection to subjects diagnosed with macular degeneration. It is envisioned that any of a number of SLPI-derived PTDs will be useful for facilitating entry not only of ranibizumab but of other selected therapeutic agents into retinal neurons.

The invention claimed is:

1. A non-native, isolated polypeptide, wherein said polypeptide functions as a protein transduction domain (PTD), and wherein said polypeptide is selected from the group consisting of SEQ ID NOS: 2 or 3.

2. A non-native, isolated polypeptide consisting of the amino acid sequence of SEQ ID NO: 2, wherein said polypeptide functions as a protein transduction domain.

3. A kit comprising the isolated polypeptide(s) of claim 1.

4. A non-native, isolated polypeptide consisting of the amino acid sequence of SEQ ID NO: 3, wherein said polypeptide functions as a protein transduction domain.

* * * * *

UNITED STATES PATENT AND TRADEMARK OFFICE
CERTIFICATE OF CORRECTION

PATENT NO. : 8,598,315 B2
APPLICATION NO. : 12/681243
DATED : December 3, 2013
INVENTOR(S) : Filbin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 685 days.

Signed and Sealed this
Twenty-second Day of September, 2015

Michelle K. Lee
*Director of the United States Patent and Trademark Office*